000
United States Patent [19]

Harper

[11] 4,312,714
[45] Jan. 26, 1982

[54] DECREASING 3-BROMO-2-BUTANONE CONTENT OF ACETIC ACID

[75] Inventor: Jon J. Harper, Naperville, Ill.

[73] Assignee: Standard Oil Company (Indiana), Chicago, Ill.

[21] Appl. No.: 104,089

[22] Filed: Dec. 17, 1979

[51] Int. Cl.$^3$ .................... C07C 51/21; C07C 51/44
[52] U.S. Cl. ................................ 203/28; 203/39; 562/549; 562/608
[58] Field of Search .................. 203/28, 29, 39; 562/608, 549

[56] References Cited

U.S. PATENT DOCUMENTS

| | | | |
|---|---|---|---|
| 2,090,941 | 8/1937 | Dreyfus et al. | 203/28 |
| 2,186,617 | 1/1940 | Othmer | 203/28 |
| 2,884,451 | 4/1959 | Graham | 562/608 |
| 3,293,292 | 12/1966 | Olivier et al. | 560/231 |
| 3,337,618 | 8/1967 | Faress | 562/608 |
| 3,578,706 | 5/1971 | List et al. | 562/414 |
| 4,111,986 | 9/1978 | Zimmerschied | 560/241 |

Primary Examiner—Wilbur L. Bascomb, Jr.
Attorney, Agent, or Firm—Fred R. Ahlers; William T. McClain; William H. Magidson

[57] ABSTRACT

The oxidation of liquid n-butane with oxygen gas at a temperature of from 120° C. up to 235° C. in the presence of an acetic acid solution containing bromide ion in combination with ions of cobalt or cobalt and manganese produces a reaction effluent containing mainly acetic acid (65 to 72 weight percent) and water (23 to 27 weight percent) together with impurity concentrations of esters and ketones boiling lower than acetic acid, higher carbon ($C_3$ and $C_4$) aliphatic monocarboxylic acids boiling higher than acetic acid and the difficultly separable 3-bromo-2-butanone impurity. The concentration of said bromoketone can be decreased by maintaining said reaction effluent or its debutanized residue at a temperature of from 150° C. up to 200° C. for 15 to 150 minutes. Subsequent distillation even further decreases the concentration of the bromoketone in the acetic acid distillate fraction.

2 Claims, No Drawings

DECREASING 3-BROMO-2-BUTANONE CONTENT OF ACETIC ACID

FIELD OF INVENTION

This invention relates to the removal of coordinate bromine from acetic acid and more particularly pertains to decreasing the content of a bromoketone from acetic acid obtained by the oxidation of liquid n-butane with oxygen gas at a temperatue of from 120° C. up to 235° C. in the presence of an acetic acid solution containing bromide ions in combination with ions of cobalt or cobalt and manganese as components of a system of catalysis.

STATE OF THE ART

Acetic acid at high selectivity can be produced at high conversion of n-butane by its oxidation as a liquid with oxygen gas at a temperature in the range of from 120° C. up to 235° C. and a gauge pressure of from 35 up to 210 kg/cm² in the presence of an acetic acid solution containing bromide ions in combination with ions of one or more transition metals as components of catalysis. According to U.S. Pat. No. 3,293,292 it is essential to use both cobalt and manganese as the transition metal component of said catalysis.

However, according to the later U.S. Pat. No. 4,111,986, the same high conversion of n-butane at high selectivity to acetic acid can be accomplished using cobalt as the sole transition metal component of said catalysis provided that for each gram mole of n-butane to be so oxidized there are employed from 1.0 up to 50 milligram equivalents of cobalt and from 2 to 50 milligram equivalents of bromine as components of the needed catalysis.

Said oxidations of n-butane produce as co-products acetate esters and ketones boiling at temperatures below the boiling point temperature of acetic acid as well as the higher carbon atom content aliphatic monocarboxylic acids propionic and butyric acid which have boiling temperatures above the boiling temperature of acetic acid. Such acetate esters, ketones and higher aliphatic acids co-products are produced in impurity level amounts and can be removed by simple distillation from the debutanized (removal of unreacted n-butane) liquid reaction effluent. Such debutanized reaction effluent contains mainly acetic acid (65 to 72 weight percent) and water (23 to 27 weight percent). However, there is one co-product produced as a result of the bromide ion component of catalysis which is difficult to remove to the impurity level which can be tolerated in acetic acid used as reactant and/or reaction solvent. It is appreciated that for some uses of acetic acid (glacial) as reactant and/or reaction solvent, that only substantially zero bromine content is acceptable but is not specified in commercial specifications.

Said difficulty separable impurity co-product has now been found to be 3-bromo-2-butanone. Its boiling temperature and that of acetic acid and of acetic acid-water compositions formed during fractionation are so close that to effect separation of said bromoketone by fractionation would require an inordinately large number of theoretical separation (tray or packing) units not acceptable for commercial operations.

Techniques have been proposed for decreasing the bromine content of acetic acid. It is not apparent from the description of such techniques that they are directed to decreasing the 3-bromo-2-butanone content of acetic acid even though there is mention of converting the bromine in organic (coordinate bound) bromides to inorganic (ionic) bromides.

According to U.S. Pat. No. 3,578,706, bromine is removed from bromine-contaminated acetic acid by stirring such contaminated acetic acid at elevated temperatures (30° to 118° C.) in the presence of a finely divided metal having an electrochemical potential between magnesium and iron, of the oxides, hydroxides, or salts of such metals and then subjecting the acetic acid so treated to ion exchange. The treatment with the metal converts organic bromides to inorganic bromides.

It might be thought that the catalytic hydrogenation technique of U.S. Pat. No. 2,884,451 for removal of odorous substances and materials of a reducing nature from acetic acid obtained by the non-catalytic oxidation of $C_4$ to $C_8$ paraffinic hydrocarbons might also convert organic bromide impurities to easily removable inorganic bromides. However, it has been found in our laboratories that such catalytic hydrogenation of a liquid phase of an organic bromide contaminated acetic acid does not suitably decrease the organic bromide contamination.

It has also been found in our laboratories that treatment of the organic bromide contaminated acetic acid with an alkali metal hydroxide, bicarbonate or carbonate and then distilling the treated acid or that treatment of the organic bromide contaminated acetic acid with a solid absorbant does not suitably decrease the organic bromide contamination. Rather it has been found that more severe treatment is necessary. For example, the organic bromide contamination can be suitably decreased by first contacting a vapor phase of the organic bromide contaminated acetic acid with hydrogen and a hydrogenation catalyst (e.g., metallic platinum or palladium per se or disposed on the surface of activated carbon) and then either (1) contacting the vapors with a bed of solid absorbant (e.g., alumina or activated carbon) or (2) condensing the treated acetic acid vapors and treating the liquid state acetic acid with an alkali metal hydroxide, carbonate or bicarbonate followed by distillative recovery of acetic acid. Such combinations of vapor phase catalytic hydrogenation of organic bromide contaminated acetic acid with solids are the subject matter of claims in the copending U. S. Pat. applications Ser. No. 970,226, now U.S. Pat. No. 4,228,307 and Ser. No. 970,222, now U.S. Pat. No. 4,227,971, both filed Dec. 18, 1978.

It has now been discovered that the 3-bromo-2-butanone contamination of acetic acid can be substantially decreased by a simple process which does not require the use of extraneous chemical compounds, specially designed apparatus, additional apparatus or unusual apparatus.

STATEMENT OF THE INVENTION

According to the present invention the decrease of the 3-bromo-2-butanone content of liquid reaction effluent or its liquid debutanized portion is accomplished by maintaining such liquid at a temperature of from 150° C. up to 200° C. under elevated pressure to maintain the debutanized effluent in the liquid phase for a period of time in the range of from 15 up to 150 minutes. After such heat treatment, distillation of the heated liquid (after debutanization of reaction effluent) will provide distillates quite low in 3-bromo-2-butanone content and a residue (still bottoms) rather high with respect to 3-bromo-2-butanone content.

The foregoing concept for decreasing the 3-bromo-2-butanone concentration is illustrated by the following examples.

EXAMPLE I

Reaction effluent is obtained from n-butane oxidation with oxygen gas conducted at a temperature of 120°–230° C. and a gauge pressure of 77 kg/cm² in the presence of 0.0025–0.01 milligram atom of cobalt and 0.0025–0.01 milligram atom of bromine per gram mole of butane. The reaction effluent is debutanized by decompressing to 21 kg/cm² and heated or cooled to 118° C. and decompressed to atmospheric pressure.

A portion of the debutanized liquid effluent is heated to 200° C. in a closed vessel for 60 minutes and then distilled into six distillate fractions and still bottoms. Each fraction taken in weight percent of charge, its total bromine content in weight percent and its 3-bromo-2-butanone (3Br-MBK) content in weight percent as well as the same bromine content of the starting material are shown in the TABLE I to follow.

TABLE I

| Fraction | Cumulative, wt. % | Total Br, wt. % | 3 BR-MEK, wt. % |
|---|---|---|---|
| 1 | 14.6 | 0.0050 | 0.01 |
| 2 | 28.4 | 0.0022 | 0.01 |
| 3 | 42.4 | 0.0034 | 0.01 |
| 4 | 56.2 | 0.0009 | N.D. |
| 5 | 70.6 | 0.0012 | N.D. |
| 6 | 84.9 | 0.0394 | N.D. |
| Still Bottoms | | 5.74 | 0.429 |
| Starting Material | | 0.81 | 0.28 |

N.D. is "none detected," meaning below analytically detectable limit.

COMPARATIVE EXAMPLE I

In contrast to the foregoing, another portion of the debutanized reaction effluent is distilled into six fractions and still bottoms. Each fraction in weight percent of charge, its total bromine content in weight percent and its 3-bromo-2-butanone (3-Br MEK) content in weight percent as well as those bromine contents of the starting material are shown in TABLE II to follow.

TABLE I

| Fraction | Cumulative, wt. % | Total Br, wt. % | 3 Br-MEK wt. % |
|---|---|---|---|
| 1 | 12.2 | 1.15 | 1.59 |
| 2 | 24.5 | 0.91 | 1.30 |
| 3 | 37.7 | 0.71 | 0.958 |
| 4 | 50.1 | 0.54 | 0.655 |
| 5 | 63.7 | 0.39 | 0.493 |
| 6 | 75.7 | 0.32 | 0.360 |
| Still Bottoms | | 1.49 | 0.251 |
| Starting Material | | 0.83 | 0.765 |

EXAMPLE II

In this example there are used two equal portions of the total reaction effluent from an n-butane oxidation with oxygen gas at 77 kg/cm² gauge pressure and 182° C. reaction temperature in the presence of 0.005 milligram mole of cobalt and 0.01 milligram mole of bromine per gram mole of butane. One portion of total reaction effluent is cooled to 150° C., divided into four alliquots, and each is held at that temperature for the time to be indicated. The second portion is cooled to 200° C., divided into four alliquots and each is held at that temperature for the time to be indicated. Each alliquot is analyzed for total ionic bromine and for 3-bromo-2-butanone (3Br-MEK) which are hereafter reported in weight percent in TABLE III to follow.

TABLE III

| | Heat Treatment | | Ionic Br, | 3 B MEK |
|---|---|---|---|---|
| | Temp., °C. | Time, min. | wt. % | wt. % |
| Sample I | | | | |
| Alliquot 1 | 150 | 10 | 0.4772 | 0.473 |
| Alliquot 2 | 150 | 20 | 0.5328 | 0.371 |
| Alliquot 3 | 150 | 40 | 0.7888 | 0.175 |
| Alliquot 4 | 150 | 80 | 0.7202 | 0.019 |
| Sample II | | | | |
| Alliquot 1 | 200 | 10 | 0.5858 | 0.234 |
| Alliquot 2 | 200 | 20 | 0.6141 | 0.055 |
| Alliquot 3 | 200 | 40 | 0.6804 | 0.016 |
| Alliquot 4 | 200 | 80 | 0.7361 | N.D. |
| Starting Material | | | 0.2122 | 0.765 |

N.D. is "none detected" meaning below detectable limit.

The foregoing data indicate that the heating of the reaction effluent caused the 3-bromo-2-butanone content to decrease and the ionic bromide content to increase. However, the loss of 3-bromo-2-butanone does appear in part as an increase of the ionic bromide content but not by an equivalent amount of HBr. Perhaps not all of the HBr resulting from debromination of 3-bromo-2-butanone caused by reaction with water

(H₂O+Br—MEK MEK+HBr)

was taken up in the liquid reaction effluent but stayed in the vapor space above the liquid even after it was cooled and thus escaped analytical detection.

All of the above eight alliquots upon distillation could provide distillates having 3-bromo-2-butanone concentrations of less than 100 ppm down to the detectable limits of present analytical techniques.

It is appreciated that the process of this invention conducted in a continuous manner, rather than the above batchwise operations, may well require, to effect the same decrease in 3-bromo-2-butanone, either longer time at the same temperature or higher temperature for the same time than shown in TABLE III.

The invention claimed is:

1. A method of decreasing the 3-bromo-2-butanone content of acetic acid obtained by the oxidation of liquid n-butane with oxygen gas at a temperature of from 120° C. up to 235° C. in the presence of an acetic acid solution containing the bromide ion in combination with ions of cobalt or cobalt and manganese followed by withdrawing fluid oxidation effluent from said oxidation, removing unreacted n-butane from the fluid effluent and distilling acetic acid from the debutanized effluent; which 3-bromo-2-butanone decreasing method comprises holding at a temperature of from 150° C. up to 200° C. for from 15 up to 150 minutes the withdrawn fluid oxidation effluent after removing unreacted n-butane.

2. A method of decreasing the 3-bromo-2-butanone content of acetic acid obtained by the oxidation of liquid n-butane with oxygen gas at a temperature of from 120° C. up to 235° C. in the presence of acetic acid solution containing the bromide ion in combination with ions of cobalt or cobalt and manganese followed by withdrawing fluid oxidation effluent from said oxidation, removing unreacted n-butane from the fluid effluent and distilling acetic acid from the debutanized effluent; which 3-bromo-2-butanone decreasing method comprises holding at a temperature of from 150° C. up to 200° C. for 15 up to 150 minutes the withdrawn fluid oxidation effluent before removing unreacted n-butane.

* * * * *

UNITED STATES PATENT OFFICE
CERTIFICATE OF CORRECTION

Patent No. 4,312,714　　　　　　　　　Dated　January 26, 1982

Inventor(s)　Jon J. Harper

It is certified that error appears in the above-identified patent and that said Letters Patent are hereby corrected as shown below:

Patent reads:

| Col. | Line | |
|---|---|---|
| 1 | 40 | "acids propionic and butyric acid" should read --acids, propionic and butyric acid,-- |
| 1 | 43 | "acids co-products" should read --acid co-products-- |
| 1 | 57 | "difficulty" should read --difficultly-- |
| 2 | 9 | "of the oxides" should read --or the oxides-- |
| 3 | 21 | "(3 Br-MBK)" should read --(3 Br-MEK)-- |
| 3 | 25 | "(3 BR-MEK)" should read --(3 Br-MEK)-- |
| 3 | 34 | "0.28" should read --0.028-- |
| 3 | 47 | "TABLE I" should read --TABLE II-- |

UNITED STATES PATENT OFFICE
CERTIFICATE OF CORRECTION

Patent No. 4,312,714          Dated January 26, 1982

Inventor(s) Jon J. Harper

It is certified that error appears in the above-identified patent and that said Letters Patent are hereby corrected as shown below:

| Col. | Line | | |
|------|------|---|---|
| 4 | 9 | "3 B MEK" should read | --3 Br-MEK-- |
| 4 | 34 | "($H_2O$+Br-MEK   MEK+HBr)" should read | --($H_2O$+Br-MEK $\longrightarrow$ MEK+HBr)-- |

Signed and Sealed this

Third Day of August 1982

[SEAL]

Attest:

Attesting Officer

GERALD J. MOSSINGHOFF

Commissioner of Patents and Trademarks